US010522254B2

(12) United States Patent
Sankaran et al.

(10) Patent No.: US 10,522,254 B2
(45) Date of Patent: *Dec. 31, 2019

(54) METHODS AND SYSTEMS FOR PREDICTING SENSITIVITY OF BLOOD FLOW CALCULATIONS TO CHANGES IN ANATOMICAL GEOMETRY

(71) Applicant: HeartFlow, Inc., Redwood City, CA (US)

(72) Inventors: Sethuraman Sankaran, Palo Alto, CA (US); Leo Grady, Millbrae, CA (US); Charles A. Taylor, Menlo Park, CA (US)

(73) Assignee: HeartFlow, Inc., Redwood City, CA (US)

( * ) Notice: Subject to any disclaimer, the term of this patent is extended or adjusted under 35 U.S.C. 154(b) by 569 days.

This patent is subject to a terminal disclaimer.

(21) Appl. No.: 15/298,964

(22) Filed: Oct. 20, 2016

(65) Prior Publication Data

US 2017/0039340 A1 Feb. 9, 2017

Related U.S. Application Data

(63) Continuation of application No. 14/596,622, filed on Jan. 14, 2015, now Pat. No. 9,501,622.

(60) Provisional application No. 61/948,325, filed on Mar. 5, 2014.

(51) Int. Cl.
| | |
|---|---|
| *G16H 50/50* | (2018.01) |
| *A61B 6/00* | (2006.01) |
| *A61B 5/00* | (2006.01) |
| *A61B 5/026* | (2006.01) |
| *G06N 3/00* | (2006.01) |
| *G06T 7/00* | (2017.01) |
| *G06F 17/18* | (2006.01) |

(52) U.S. Cl.
CPC ............ *G16H 50/50* (2018.01); *A61B 5/7267* (2013.01); *A61B 6/00* (2013.01); *A61B 6/507* (2013.01); *A61B 6/5217* (2013.01); *G06F 17/18* (2013.01); *G06N 3/00* (2013.01); *G06T 7/0012* (2013.01); *A61B 5/026* (2013.01); *A61B 2576/02* (2013.01); *G06T 2207/30104* (2013.01)

(58) Field of Classification Search
None
See application file for complete search history.

(56) References Cited

U.S. PATENT DOCUMENTS

| 8,315,812 | B2 | 11/2012 | Taylor |
| 2014/0039276 | A1 | 2/2014 | Hattangadi |
| 2014/0073976 | A1 | 3/2014 | Fonte |
| 2014/0073977 | A1 | 3/2014 | Grady |
| 2014/0249784 | A1 | 9/2014 | Sankaran |

FOREIGN PATENT DOCUMENTS

WO   WO 2013/138428   9/2013

OTHER PUBLICATIONS

U.S. Appl. No. 14/231,870, filed Apr. 1, 2014 entitled "Systems and Methods for Using Geometry Sensitivity Information for Guiding Workflow".
Sankaran et al. "Fast Computation of Hemodynamic Sensitivity to Lumen Segmentation Uncertainty." Jun. 16, 2015, (11 pages).
Sankaran et al. (Journal of Biomechanical Engineering (2011) vol. 133:1-12).
Sankaran, "Fast computation of hemodynamic sensitivity to lumen segmentation Uncertainty"; Transactions on Medical Imaging (10 pages).
Search Report dated Jun. 1, 2015; issue in International application No. PCT/US2015/017471 (5 pages).
Sankaran et al. (Physics of Fluids (2010) vol. 22:121902:1-16; available online Dec. 22, 2010).

*Primary Examiner* — Lori A. Clow
(74) *Attorney, Agent, or Firm* — Bookoff McAndrews, PLLC (57) ABSTRACT

Embodiments include methods and systems for determining a sensitivity of a patient's blood flow characteristic to anatomical or geometrical uncertainty. For each of one or more of individuals, a sensitivity of a blood flow characteristic may be obtained for one or more uncertain parameters. An algorithm may be trained based on the sensitivities of the blood flow characteristic and one or more of the uncertain parameters for each of the plurality of individuals. A geometric model, a blood flow characteristic, and one or more of the uncertain parameters of at least part of the patient's vascular system may be obtained for a patient. The sensitivity of the patient's blood flow characteristic to one or more of the uncertain parameters may be calculated by executing the algorithm on the blood flow characteristic of at least part of the patient's vascular system, and one or more of the uncertain parameters.

20 Claims, 7 Drawing Sheets

METHODS AND SYSTEMS FOR PREDICTING SENSITIVITY OF BLOOD FLOW CALCULATIONS TO CHANGES IN ANATOMICAL GEOMETRY

RELATED APPLICATIONS

This application is a continuation of U.S. application Ser. No. 14/596,622, filed Jan. 14, 2015, which claims the benefit of priority from U.S. Provisional Application No. 61/948,325, filed Mar. 5, 2014, all of which are incorporated herein by reference in their entireties.

TECHNICAL FIELD

Embodiments of the present disclosure relate to methods and systems for patient-specific modeling of blood flow and, more particularly, to methods and systems for sensitivity analysis in patient-specific modeling of blood flow.

BACKGROUND

Coronary artery disease is a very common ailment that affects millions of people annually. While significant strides have been made in the treatment of coronary artery disease, including the use of percutaneous coronary intervention (PCI) and coronary artery bypass graft surgery (CABG), a good understanding of the pathogenesis and the mechanism of the disease is still lacking.

Coronary artery disease may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

A need exists to provide more accurate data relating to coronary lesions, for example, size, shape, location, functional significance (e.g., whether the lesion impacts blood flow), etc. Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). These noninvasive tests, however, typically do not provide a direct assessment of coronary lesions or assess blood flow rates. The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers).

For example, anatomic data may be obtained noninvasively using coronary computed tomographic angiography (CCTA). CCTA may be used for imaging of patients with chest pain and involves using computed tomography (CT) technology to image the heart and the coronary arteries following an intravenous infusion of a contrast agent. However, CCTA also cannot provide direct information on the functional significance of coronary lesions, for example, whether the lesions affect blood flow. In addition, since CCTA is purely a diagnostic test, it can neither be used to predict changes in coronary blood flow, pressure, or myocardial perfusion under other physiologic states (e.g., exercise).

Thus, patients may require an invasive test, such as diagnostic cardiac catheterization, to visualize coronary lesions. Diagnostic cardiac catheterization may include performing conventional coronary angiography (CCA) to gather anatomic data on coronary lesions by providing a doctor with an image of the size and shape of the arteries. CCA, however, does not provide data for assessing the functional significance of coronary lesions. For example, a doctor may not be able to diagnose whether a coronary lesion is harmful without determining whether the lesion is functionally significant. Thus, CCA has led to a procedure referred to as an "oculostenotic reflex," in which interventional cardiologists insert a stent for every lesion found with CCA regardless of whether the lesion is functionally significant. As a result, CCA may lead to unnecessary operations on the patient, which may pose added risks to patients and may result in unnecessary heath care costs for patients.

During diagnostic cardiac catheterization, the functional significance of a coronary lesion may be assessed invasively by measuring the fractional flow reserve (FFR) of an observed lesion. FFR may be defined as the ratio of the mean blood pressure or flow downstream of a lesion divided by the mean blood pressure or flow upstream from the lesion, for example, the aortic pressure, under conditions of increased coronary blood flow, for example, when induced by intravenous administration of adenosine. Blood pressures may be measured by inserting a pressure wire into the patient. Thus, the decision to treat a lesion based on the determined FFR may be made after the initial cost and risk of diagnostic cardiac catheterization has already been incurred.

To reduce the above disadvantages of invasive FFR measurements, HeartFlow Inc. has developed methods for assessing coronary anatomy, myocardial perfusion, and coronary artery flow noninvasively. Specifically, computational fluid dynamics (CFD) simulations have been successfully used to predict spatial and temporal variations of flow rate and pressure of blood in arteries, including FFR. Such methods and systems benefit cardiologists who diagnose and plan treatments for patients with suspected coronary artery disease, and predict coronary artery flow and myocardial perfusion under conditions that cannot be directly measured, for example, exercise, and to predict outcomes of medical, interventional, and surgical treatments on coronary artery blood flow and myocardial perfusion.

However, computational modeling of hemodynamics involves a reconstructed geometry of the patients' arteries, which is facilitated through high-resolution imaging. For example, many CFD frameworks for noninvasively calculating FFR assume that: (i) the geometry is known with certainty, (ii) clinical variables such as blood pressure, hematocrit, myocardial mass, etc. are known with certainty, and/or (iii) boundary conditions at the inlet and outlets of the computational model are known with certainty. However, in reality, the FFR predicted using CFD varies based on the accuracy of the available data and mathematical models that describe hemodynamics in the arteries. As a result, there is a need for methods and systems for incorporating and quantifying the effects of uncertainties in the available data, as well as mathematical models. In addition, there is a need for methods and systems for assigning confidence intervals to determined FFR values as well as ranking the sensitivity of FFR calculation to the possible values of different parameters.

The foregoing general description and the following detailed description are exemplary and explanatory only and are not restrictive of the disclosure.

SUMMARY

Embodiments discussed herein broadly concern predicting sensitivities of blood flow calculations to changes in an anatomical geometry. A digital representation, such as a scan of a patient's heart, often contains imperfections, or uncertainties. These uncertainties may affect various resulting blood flow calculations to a great degree, or possibly not much at all. The degree to which uncertainties in a digital representation, such as a heart scan, affect resulting blood flow calculations may be called the sensitivity. For example, if a scan of a patient's heart contains an artifact such as misalignment, motion, blooming, etc., and that artifact results in large errors in blood flow calculations that are made based on the scan, then the sensitivity is high. As discussed in various embodiments herein, machine learning and other algorithms may be used to predict various sensitivities, and hence the confidence a physician or technician may place in blood flow calculations for a given patient.

In accordance with an embodiment, methods are disclosed for predicting geometric sensitivity, using at least one computer system. One method determines a sensitivity of a patient's blood flow characteristic to anatomical or geometrical uncertainty, the method comprising: obtaining, for each of a plurality of individuals, a sensitivity of a blood flow characteristic to one or more uncertain parameters; training a machine-learning algorithm based on the sensitivities of the blood flow characteristic and one or more of the uncertain parameters for each of the plurality of individuals; obtaining, for a patient, a geometric model, a blood flow characteristic, and one or more of the uncertain parameters of at least part of the patient's vascular system; and calculating a sensitivity of the patient's blood flow characteristic to one or more of the uncertain parameters by executing the machine-learning algorithm on the blood flow characteristic of at least part of the patient's vascular system, and one or more of the uncertain parameters.

In accordance with another embodiment, a method is disclosed for predicting geometric sensitivity, using at least one computer system, the method comprising: receiving a first digital representation of a first physical system; determining at least one uncertainty of at least one property of the first digital representation; calculating at least one sensitivity for the uncertainty using a stochastic algorithm; determining a machine learning predictor using data from a plurality of patients; and predicting sensitivities for a second digital representation of a second physical system using the machine learning predictor.

In accordance with another embodiment, a system is disclosed for predicting geometric sensitivity, the system comprising: a data storage device storing instructions for predicting geometric sensitivity; and a processor configured to execute the instructions to perform a method including the steps of: receiving a first digital representation of a first physical system; determining at least one uncertainty of at least one property of the first digital representation; calculating at least one sensitivity for the uncertainty using a stochastic algorithm; determining a machine learning predictor using the at least one sensitivity; and predicting sensitivities for a second digital representation of a second physical system using the machine learning predictor.

In accordance with another embodiment, a non-transitory computer readable medium for use on at least one computer system containing computer-executable programming instructions for predicting geometric sensitivity, the method comprising: receiving a first digital representation of a first physical system; determining at least one uncertainty of at least one property of the first digital representation; calculating at least one sensitivity for the uncertainty using a stochastic algorithm; determining a machine learning predictor using the at least one sensitivity; and predicting sensitivities for a second digital representation of a second physical system using the machine learning predictor.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate several embodiments and together with the description, serve to explain the principles of the disclosure.

DESCRIPTION OF THE EMBODIMENTS

Reference will now be made in detail to the exemplary embodiments of the invention, examples of which are illustrated in the accompanying drawings.

In an exemplary embodiment, a method and system determines information relating to blood flow in a specific patient using information retrieved from the patient noninvasively. Various embodiments of such a method and system are described in greater detail in U.S. Pat. No. 8,315,812 ("the '812 patent"), filed Jan. 25, 2011, and entitled "Method and System for Patient-Specific Modeling of Blood Flow," which is hereby incorporated herein by reference in its entirety.

In some embodiments, the information determined by the method and system may relate to blood flow in the patient's coronary vasculature. Alternatively, the determined information may relate to blood flow in other areas of the patient's vasculature, such as carotid, peripheral, abdominal, renal, and cerebral vasculature. The coronary vasculature includes a complex network of vessels ranging from large arteries to arterioles, capillaries, venules, veins, etc. The coronary vasculature circulates blood to and within the heart and includes an aorta that supplies blood to a plurality of main coronary arteries (e.g., the left anterior descending (LAD) artery, the left circumflex (LCX) artery, the right coronary (RCA) artery, etc.), which may further divide into branches of arteries or other types of vessels downstream from the aorta and the main coronary arteries. Thus, the exemplary method and system may determine information relating to blood flow within the aorta, the main coronary arteries, and/or other coronary arteries or vessels downstream from the main coronary arteries. Although the aorta and coronary arteries (and the branches that extend therefrom) are discussed below, the disclosed method and system may also apply to other types of vessels.

In an exemplary embodiment, the information determined by the disclosed methods and systems may include, but is not limited to, various blood flow characteristics or parameters, such as blood flow velocity, pressure (or a ratio thereof), flow rate, and FFR at various locations in the aorta, the main coronary arteries, and/or other coronary arteries or vessels downstream from the main coronary arteries. This information may be used to determine whether a lesion is functionally significant and/or whether to treat the lesion. This information may be determined using information obtained noninvasively from the patient. As a result, the decision whether to treat a lesion may be made without the cost and risk associated with invasive procedures.

As described above, the above-described techniques for computational modeling for noninvasively calculating FFR may assume that: (i) the geometry is known with certainty, (ii) clinical variables such as blood pressure, hematocrit, myocardial mass, etc. are known with certainty, and/or (iii) boundary conditions at the inlet and outlets of the computational model are known with certainty. However, in reality, the FFR predicted using CFD varies based on the accuracy of the available data and mathematical models that describe hemodynamics in the arteries. Accordingly, the present disclosure also describes methods and systems for incorporating and quantifying the effects of uncertainties in the available data, as well as mathematical models. In addition, the present disclosure describes methods and systems for determining FFR values, as well as rank the sensitivity of FFR calculations to different parameters. In one embodiment, the present disclosure incorporates the sensitivity analysis techniques disclosed in U.S. patent application Ser. No. 13/864,996 ("the '996 application"), filed on Apr. 17, 2013, the entire disclosure of which is incorporated herein by reference. In another embodiment, the present disclosure incorporates the sensitivity analysis techniques disclosed in U.S. patent application Ser. No. 14/231,870 ("the '870 application"), filed on Apr. 1, 2014, the entire disclosure of which is incorporated herein by reference.

In contrast to and addition to the '996 application, the present disclosure describes various methods for using machine learning and other algorithmic techniques for performing sensitivity analysis, including defining input uncertainties, and calculating FFR analysis sensitivities, according to a general and several specific exemplary embodiments. Sensitivities of determined blood flow characteristics, such as FFR, to uncertain parameters, uncertain clinical variables, and/or uncertain geometries may thus be determined more quickly by relying on machine learning techniques trained based on relatively large databases or data sets of training data of patient geometric sensitivity.

It should be appreciated that blood flow modeling in the coronary arteries may be performed by solving the Navier-Stokes equations, which are partial differential equations describing blood velocity and pressure. Computational fluid dynamics (CFD) simulations may be used to predict spatial and temporal variations of flow rate and pressure of blood in arteries, including FFR. CFD simulations may rely on (i) an accurate reconstruction of the coronary artery geometry from a CT scan, (ii) an accurate representation of the system properties such as blood viscosity, aortic pressure, flow-split across different arteries, etc., and (iii) accurate enforcement of boundary conditions, which describe the properties of a microvascular coronary bed that is not modeled. In practice, it may not be possible to obtain the properties mentioned above with certainty. Hence, it may be useful to quantify the uncertainty, for example by calculating the standard deviation and higher statistical moments including confidence intervals of FFR.

Stochastic Navier-Stokes equations may be used to solve for many types of velocity and pressure variables that depend on a stochastic, or probabilistic, dimension, in addition to space and time. The computational complexity depends on the problem and the number of sources of uncertainties that are accounted for. If the reconstructed geometry is stochastic, then the number of stochastic dimensions could easily be of the order of 50 to 100. Since solving the deterministic Navier-Stokes equations themselves is computationally intensive and could involve significant processing time depending on the size of the coronary tree, traditional methods, such as Monte-Carlo, can be inefficient and impractical to use. Classes of techniques called "stochastic collocation methods" may be highly efficient in quantifying uncertainty. However, they still require hundreds of simulations translating to significant computational Stochastic effort.

Embodiments disclosed herein may include using a machine learning predictor as a surrogate for calculating FFR. This may be achieved by defining patient-specific features, and computing a map between these features and FFR by training on a large database of patients for which CFD results have been computed. An extensive set of features may be chosen encompassing geometric, clinical, and analytical model based features, such as analytical solutions for pipe flow parameterized by pipe radii, flow rate, viscosity, and the length of the pipe. This makes the uncertainty quantification problem tractable, reducing the computational time for the stochastic algorithm to approximately from days to under an hour. However, it is desirable to reduce this time further so that real time computation of sensitivity is possible.

More specifically, the techniques presented herein may utilize a database of patient-specific sensitivities to construct a machine learning predictor for calculating sensitivities. This machine learning predictor may encode the stochastic collocation algorithm in addition to the Navier-Stokes equation. In addition to the features used for calculating FFR (discussed in the '812 patent and '996 application referenced and incorporated herein above), the following additional features may be added: (i) magnitude of input uncertainty;

(ii) FFR calculated using machine learning; and (iii) geometry parameterization. In one embodiment, FFR may be calculated using machine learning according to any of the techniques disclosed in U.S. patent application Ser. No. 13/895,893, filed May 16, 2013, by Grady, Choi, and Singer, and Ser. No. 13/895,871, filed May 16, 2013, by Fonte, Choi, Grady, and Singer, the entire disclosures of which are hereby incorporated herein by reference.

Since geometry parameterization may be used as an input feature, arbitrary spatial resolution in sensitivity can be achieved with almost no additional cost. This method can be used for calculating sensitivity to geometry in other applications, such as sensitivity of drag and lift forces to airfoil shape, sensitivity of wall shear stress to stent deployment geometry, sensitivity of drilling location to uncertainty in dispersion index using flow simulations in porous media, etc.

Figure 1:
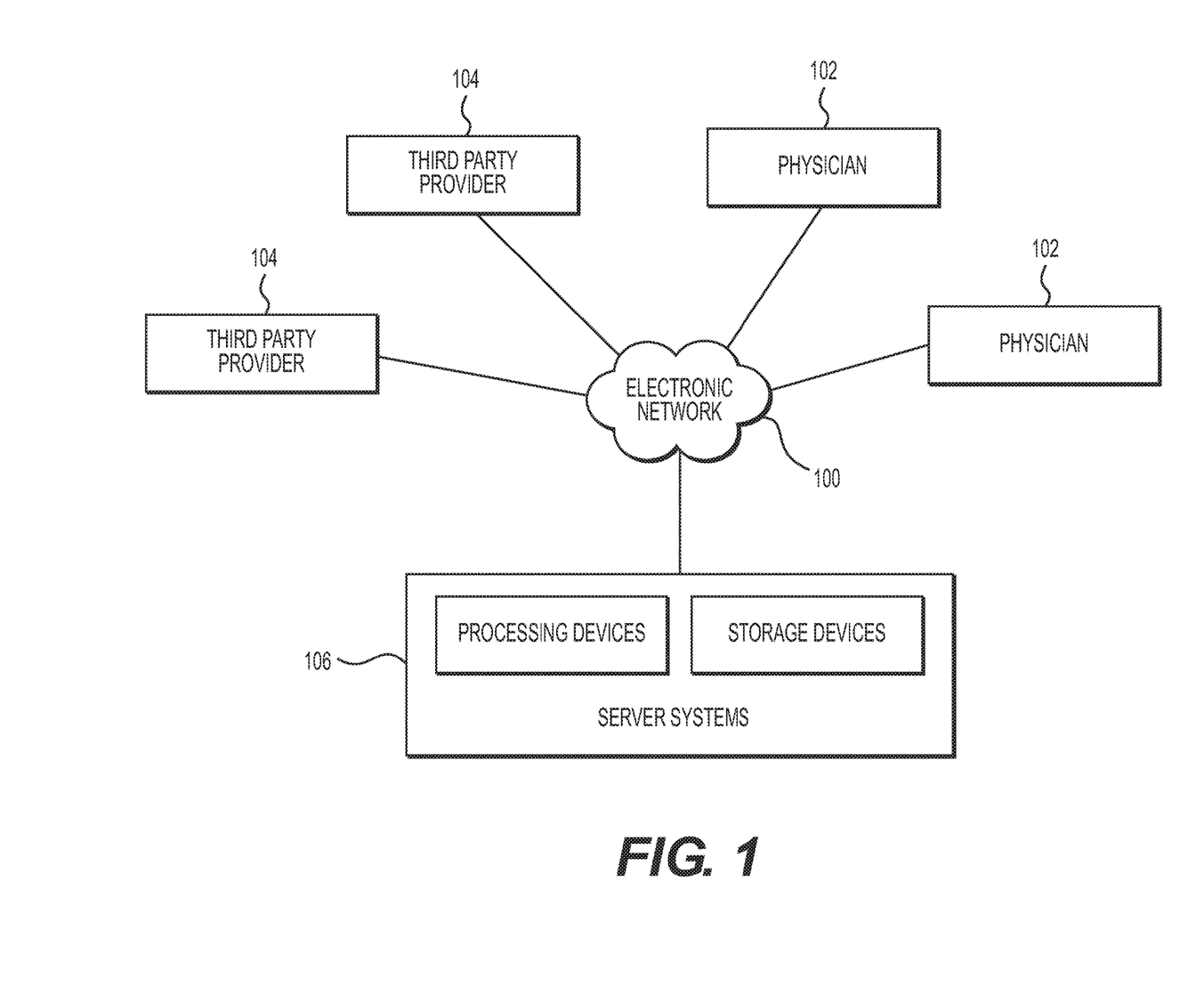
FIG. 1 is a block diagram of an exemplary system and network for predicting sensitivity of blood flow calculations to changes in anatomical geometry, according to an exemplary embodiment of the present disclosure.

Referring now to the figures, FIG. 1 depicts a block diagram of a exemplary methods and systems for predicting sensitivity of blood flow calculations to changes in anatomical geometry. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of at least a portion of the anatomy of a plurality of individuals, and of at least one patient. For example, physicians 102 and/or third party providers 104 may create or otherwise obtain images of at least a portion of one or more individuals' and/or patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices.

Figure 2:
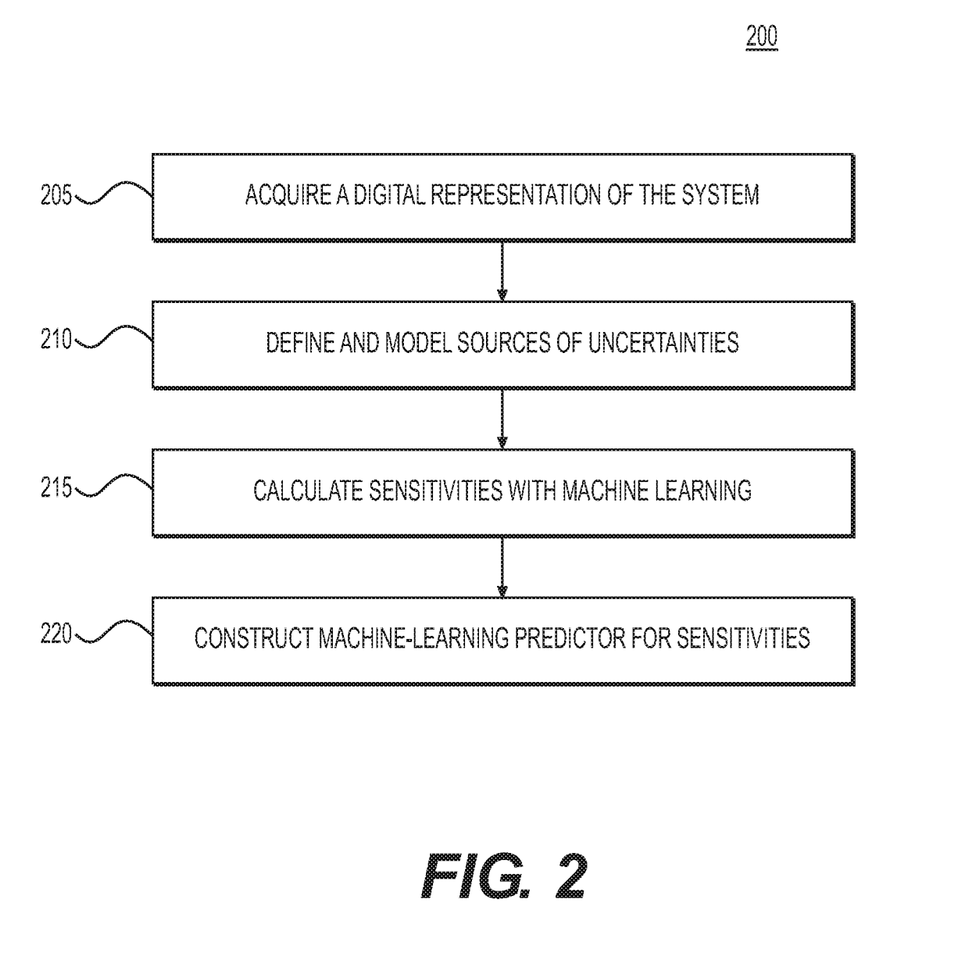
FIG. 2 is a flow chart that describes an exemplary process for geometric sensitivity prediction, according to an exemplary embodiment of the present disclosure.

An exemplary general embodiment will next be described, with reference to FIG. 2, followed by several specific embodiments. As shown in the embodiment 200, sources of uncertainties associated with a digital representation may be determined, and machine learning, or other algorithms, such as lookup tables, may be used to predict one or more sensitivities.

As shown in step 205, a digital representation of the system may first be acquired, for example, of a system that is to be studied. This could include image-based representation, measured variables, a list, or a table of parameter values and features representative of the system, or a combination of the above. The system may then be isolated to be studied. This may be done by delineating the geometry, system properties, and specific conditions. This could include additional steps such as image processing and reconstructing the system from a raw digital representation.

Sources of uncertainties may then be defined and modeled, as shown in step 210. Uncertainties in the geometry, system properties, and/or conditions imposed, which are relevant to the quantities of interest, may be defined. Uncertainty can be associated with an entity based on (a) inherent noise in the measurement or acquisition of the entity, (b) uncertainty in the algorithm to delineate the entity from digital representation, and/or (c) uncertainty due to the discrete representation of a dynamic system (e.g., using a finite set of static snapshots to represent the system). A form of probability distribution function (pdf) may be assigned to each of the entities defined above. The form of pdf could be motivated by understanding the cause and source of uncertainty, empirical data, and/or physical reasoning. Commonly used pdfs are Gaussian and Uniform distributions.

Sensitivities may be calculated using machine learning, as shown in step 215. The geometry may be parameterized by splitting the geometry of the system into multiple regions. Each such split may be eventually assigned a sensitivity value. Correlations between different regions in the geometry can also be modeled. This split can be performed either using salient locations of the system which encode different physical properties and/or features of the system, and/or simply to achieve a desired resolution in sensitivity. A stochastic algorithm may also be initialized. An adaptive stochastic collocation algorithm may be utilized to compute specific instances of entities where simulations may be performed to calculate the quantity of interest. For example, the stochastic collocation algorithm may compute instances of geometry from a probabilistic space of geometries using quadrature points identified by the Smolyak sparse grid algorithm. Sensitivities may also be calculated by solving the stochastic system. Sensitivities may be calculated by running the simulations at quadrature points identified in during the initialization of the stochastic algorithm. These simulations can be run by either using computational methods by discretizing the geometry and solving partial differential equations (e.g. finite element methods), or by using surrogate functions such as the response surface method, reduced order models, machine learning, etc.

As shown in step 220, a machine-learning predictor may also be constructed for sensitivities. Available data may be split into a training and test set. The dataset may be split where sensitivities were calculated, by solving the stochastic system, into a training and test set. A random split of 66% training set and 34% test set may be useful, though other pre-determined splits may also be used.

While in training mode, features may be defined and calculated. Problem-specific features that are important in the calculation of sensitivities may be defined. These include (a) problem-specific geometric features, such as spatial variation in area and diameter, branching features (location/size of nearest branch), volumetric features (e.g. total volume upstream or downstream of a given location for flow simulations); (b) problem-specific variables or parameters, such as viscosity or density (for flow problems), constitutive material properties for solid mechanics problems, dispersivity for flow in porous media etc.; and/or (c) stochastic variables, such as the magnitude of input uncertainty, the form of input uncertainty, and the parameterization of the geometry into independent random variables (number of stochastic dimensions). Mathematical transformation of the features may be performed. For example, mathematical transformations, such as squaring, can improve the separation of feature values and hence, prediction error. Optimal regressor(s) may also be calculated. One or more optimal machine learning regressors may be determined from at least one regressor candidate. These could include linear regression models, non-linear polynomial models, decision trees, M5 rules (terminal leaves of decision trees have a linear regression model), etc. Bootstrap aggregating may also be used to improve performance. The regressor may also be saved to a digital representation (e.g., the memory or digital storage [e.g., hard drive, network drive] of a computational device such as a computer, laptop, DSP, server, etc.).

In a production mode, data may be obtained for at least one new representation of the system. The saved regressor from training may be to calculate sensitivities for the new digital representation.

Figure 3:
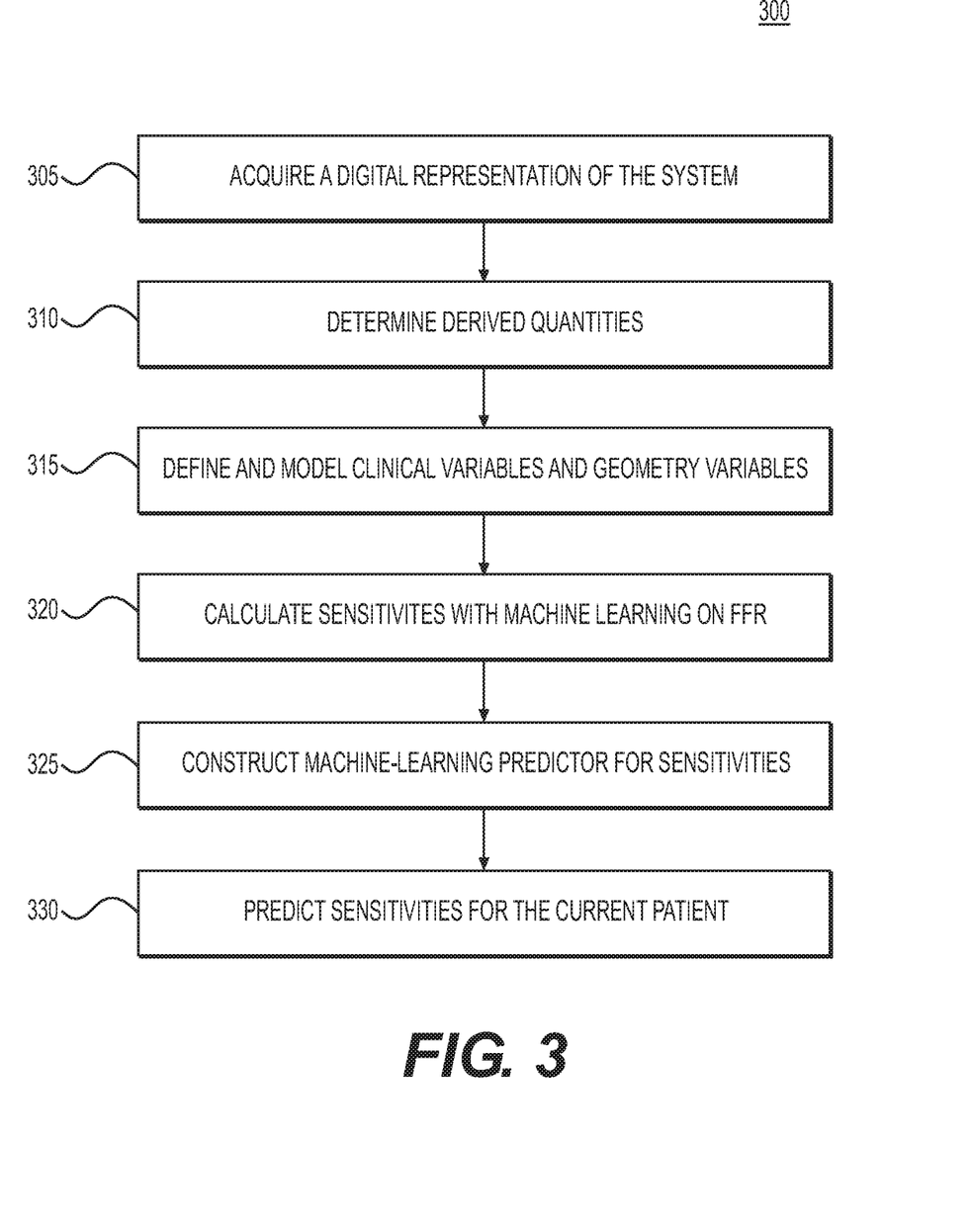
FIG. 3 is a flow chart that describes an exemplary process for sensitivity analysis in patient-specific modeling of blood flow, according to an exemplary embodiment of the present disclosure.

A specific exemplary embodiment of the present disclosure for sensitivity analysis in patient-specific modeling of blood flow will now be discussed, with reference to FIG. 3. As shown in the embodiment 300, sources of uncertainties associated with a digital representation may be determined, and machine learning, or other algorithms, may be used to predict one or more sensitivities for the current patient.

As shown in step 305, for one or more patients, a digital representation may be acquired (e.g., the memory or digital storage [e.g., hard drive, network drive] of a computational device such as a computer, laptop, DSP, server, etc.) and processed. The digital representation may include, for example, an image scan of the patient that includes the ascending aorta and/or coronary artery tree. The type of image scan could include a cardiac computed tomography (CCTA), MRI, ultrasound etc. Using the image scan, a digital representation that encompasses regions of interest may isolated. Centerlines, which pass through the center of vessels of interest, may be computed. Subsequently, these may be used to construct lumen segments manually or automatically to identify voxels belonging to the aorta and to the lumen of the coronary arteries. Once all relevant voxels are identified, a geometric model of the aorta and relevant coronary arteries may be reconstructed. In addition to a CCTA, etc., a set of clinical parameters may be measured or obtained which include heart-rate, systolic and diastolic brachial blood pressures, hematocrit, patient height and weight, and patient history such as smoking status, presence/absence of diabetes, etc.

Based upon the image scan and the reconstructed geometric model, a set of derived quantities may be calculated, as shown in step 310. These derived quantities may include: (a) myocardial mass($m_{myo}$), which may be obtained by image segmentation of the left ventricle to calculate the volume of myocardium and multiplying it with a blood density; (b) body surface area, which may be calculated from the patient height (h) and weight (w) as $$BSA = \sqrt{\frac{hw}{3600}};$$

(c) viscosity, which may be calculated from the hematocrit (hem) as $$\eta = \frac{c}{\left(1 - \frac{hem}{100}\right)^{2.5}}$$

where c may be 0.0012; (d) inlet aortic flow rate (Q), which may be calculated from scaling studies as $$Q = \frac{1}{60} BSA^{1.15};$$

(e) coronary flow rate ($q_{cor}$), which may be calculated from myocardial mass as $$q_{cor} = c_{dil} \frac{5.09}{60} m_{myo}^{0.75}$$

where $c_{dil}$ is the dilation factor; (f) coronary resistance, where the net coronary resistance may be calculated from the desired coronary flow, and the value for individual outlets is calculated based on their areas; and/or (g) resistance of outlet aorta, which may be calculated based on aortic pressure, aortic flow rate and/or desired coronary flow rate, for example.

For each patient that underwent CCTA, the input uncertainties may be identified and modeled, as shown in step 315. Derived quantities such as clinical parameters from step 310 may be modeled using (i) uniform probability distribution function if only the range of the parameter is known, and/or (ii) Gaussian probability distribution function, if a mean and standard deviation are known. Geometry variables, such as the surface of the geometry, and consequently lumen area and wall boundaries may also be considered uncertain. The number of stochastic geometric variables may depend on how the geometry is discretized. The training and test modes may be discretized differently. In the training mode, each segment between two branch locations may be considered an independent random variable. In the test mode, the discretization could be made as fine as possible, such as, for example, every set of six centerline points can be considered an independent variable.

Sensitivity data may be computed using machine learning on FFR, as shown in step 320. Sensitivity data may be calculated on an online and/or offline database of patient geometries. For each patient-specific data in the database, one or more geometric features, features from clinical data, and/or hemodynamic features may be calculated. Geometric features may include calculating or obtaining lumen area, lumen diameter, volume of blood upstream and downstream, distance to nearest bifurcation upstream and downstream, distance to ostium (location where aorta meets coronary artery), min/max/mean upstream and downstream diameter, distance to minimum upstream and downstream diameter, number of upstream and downstream bifurcations, average upstream and downstream diameter, min/max/mean area of all downstream outlets, min/max/mean outlet resistances, area of next centerline point, and/or total and mean downstream geometric resistance. Features from clinical data may include calculating or obtaining the viscosity of blood, systolic and diastolic pressures, body surface area, and/or estimates of aortic and coronary blood flow rate. Hemodynamic features may also be calculated or obtained, which may include flow rates, pressure drops, and FFR using Poiseulle's equation, kinetic energy drop, and/or pressure recovery factor (which may be defined as the ratio of downstream to upstream area if this ratio is >1.2, although this pre-determined ratio may vary).

FFR values may be calculated by performing 3D blood flow simulations by solving Navier-Stokes equations for patients in a database, such as an offline database.

A machine-learning predictor may be calculated for FFR. The database may be divided into, for example, a 66% training set and 34% test set. This pre-determined division may vary. The method may further include computing a decision tree that maps the features previously identified in step 320 and the simulation results, so that predictive error is minimized. The resulting predictor may be stored in digital form (e.g., disc, laptop, hard-drive, etc.).

Sensitivities may also be calculated. Quadrature points may be calculated for performing uncertainty quantification using the Smolyak algorithm. Each quadrature point to a feature set listed above may be mapped. For each quadrature point, FFR may be evaluated using a machine learning predictor previously calculated. Lagrange polynomial interpolates may be used to interpolate FFR in the stochastic space, and by sampling the stochastic space and constructing, for example, a histogram, the standard deviation in FFR (sensitivity) may be calculated.

As shown in step 325, a machine-learning predictor for sensitivity may also be calculated (e.g., using one or more offline databases). A feature vector, from step 320, may be enriched. The following features may be used to predict sensitivity in addition to those listed above in regards to step 320—(i) length of independent geometric segments, (ii) magnitude of input uncertainty, and/or (iii) FFR calculated using machine learning, as well as non-linear transformations of the above such as square, square root, log, etc. A machine-learning predictor may be calculated. The one or more databases may be divided into a pre-determined ratio, for example, a 66% training set and 34% test set, although this division may vary. A decision tree may also be computed that maps the features identified in the enriched feature vector to the sensitivities calculated in step 320, so that predictive error is minimized. The resulting predictor may be stored in digital form (e.g. disc, laptop, hard-drive, etc.).

As shown in step 330, sensitivities may be predicted for at least one current patient. Sensitivities for the patient data stored in step 305 and 310 may be predicted by first calculating all the features identified in step 325, and using the stored machine learning predictor, from step 325, to calculate sensitivities through the patient specific model. A multi-resolution analysis may also be performed. Desired spatial resolution may be achieved by defining segment size based on the desired resolution. Six centerline points may be chosen to define a segment, for example. Hence, a spatial resolution of 3 mm could be achieved if the distance between centerline points is 0.5 mm (see FIG. 6).

Figure 4:
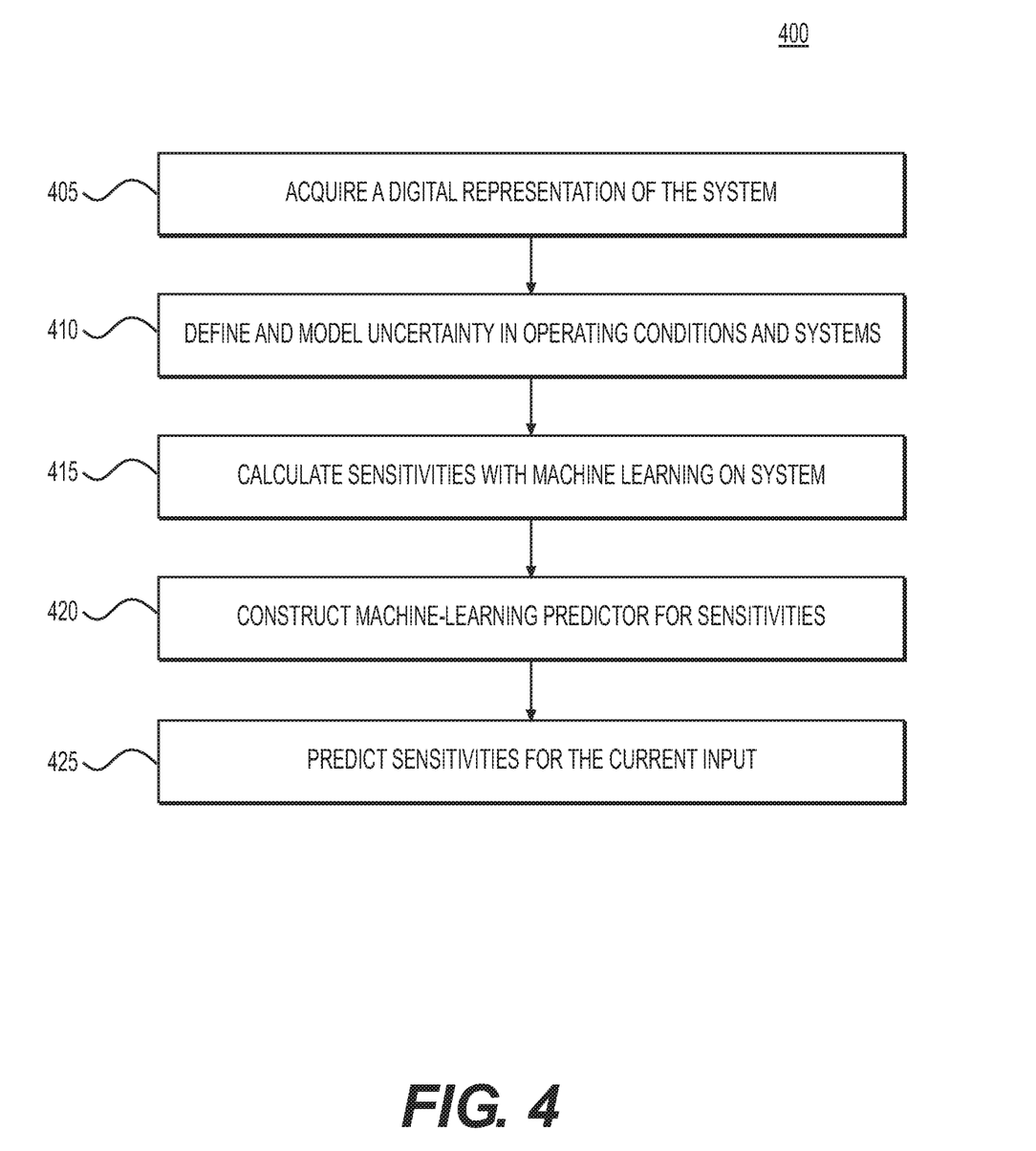
FIG. 4 is a flow chart that describes an embodiment for sensitivity of lift and drag forces to airfoil shape, according to an exemplary embodiment of the present disclosure.

An exemplary embodiment of the method to calculate the sensitivity of lift and drag forces to airfoil shape is now described, with reference to FIG. 4. This has implications in the predictive modeling of drag and lift variability due to airfoil shape, as well as to the optimal design of aircraft wings. As shown in the embodiment 400, sources of uncertainties associated with a digital representation or one or more airfoils may be determined, and machine learning, or other algorithms, may be used to predict one or more sensitivities for the airfoil data.

As shown in step 405, input data may be acquired and processed. The input data may comprise the shape of the airfoil to be studied. This could be in the form of an analytical function, free form representation using a set of control points or some other representation such as a Bezier or B-Spline control point representation. The quantity of interest may also be acquired and analyzed. This could be overall lift and drag forces on the aircraft, and/or localized forces on specific points in the aircraft wing, and/or other forces on the aircraft.

As shown in step 410, sources of uncertainties may be defined and modeled. The model of uncertainty may be split into uncertainty in operating conditions and uncertainty in shape. Regarding uncertainty in operating conditions, aircrafts operate under widely varying conditions such as air temperature, density and head or tail winds, and/or loading conditions. The goal is to operate safely and efficiently under a wide range of these conditions. The roll and yaw of aircraft could also be temporarily compromised or vary during flight. A Gaussian distribution in the operating conditions may be assumed, and nominal temperature and absence of head or tail winds on average may also be assumed. Regarding uncertainty in shape, the shape of an aircraft wing can be uncertain due to uncertainty in the manufacturing process or large deformation under unexpected operating conditions. Sensitivity to shape is also a useful metric when performing shape optimization for airfoil design. A stochastic space of candidate shapes may be determined.

The sensitivity may be calculated, for example, using an online and/or offline database, as shown in step 415. A database containing a large number of airfoil shapes may be obtained. This may encompass airfoils with different shapes. When running one or more simulations, lift and drag forces on the airfoil may be calculated by solving Navier-Stokes equations for air velocity and pressure near the wall of the airfoil. No slip boundary conditions may be enforced at the wall of the airfoil. A computational mesh of the air surrounding the airfoil may be created, with a boundary layer mesh surrounding the air foil to account for steep changes in air velocity and pressure. The sensitivity may also be calculated using adjoint equations.

Analytical equations for sensitivities may be computed by deriving adjoint equations from governing Navier-Stokes equations. These equations are usually solved backwards in time, and have a heavy computational demand (may need to store the history of the solution at all times) but are feasible to calculate in some situations. Solutions of these equations provide information about sensitivity at all points in space. When it is not feasible to solve adjoint equations, a stochastic collocation method can be used.

Further, the sensitivity may be calculated using stochastic collocation. A stochastic space representing uncertainty in operating conditions and shape may be defined. Navier-Stokes equations from above may be solved at quadrature points identified by the stochastic collocation algorithm. The velocity and pressure of air may be calculated throughout the stochastic space using Lagrange polynomial interpolation. A histogram may be constructed by sampling the stochastic space according to the input probability defined in step 410, from which sensitivity values are calculated.

As shown in step 420, a machine learning predictor for sensitivity may be calculated. Regarding input features, for each airfoil shape, the set of input features may be computed, such as the number of control points, shape coefficients, the magnitude of input uncertainty, and/or loading conditions. The number of control points may be points that define the geometry of the airfoil. The shape coefficients are, for example, coefficients in the analytical representation of the airfoil shape. These could be the coefficients of Bezier curves, or piecewise polynomial coefficients. The magnitude of input uncertainty defined in step 415 may also be computed. The loading conditions may also be computed, such as the weight of the aircraft, head and tail wind forces, and thrust generated by the aircraft.

The database may be divided into a 66% training set and 34% test set, although this pre-determined split may vary. A decision tree may be computed, or a polynomial regressor that maps the input features identified above to the sensitivities calculated in step 415, so that predictive error is minimized. The resulting predictor may be stored in digital form (e.g. disc, laptop, hard-drive, network storage, etc.).

The sensitivities for the current input may then be predicted, as shown in step 425. The sensitivities for the airfoil data stored in step 405 may be predicted by first calculating all the features identified in step 420, and using the stored machine learning predictor from step 420 to calculate sensitivities through the patient specific model. The solution may be mapped and displayed. The sensitivity of lift and drag forces may be mapped to shape coefficients, to the sensitivity with respect to the geometry. Store the maximum sensitivity at each discretized point in the geometry, and display the results in a display device.

Figure 5:
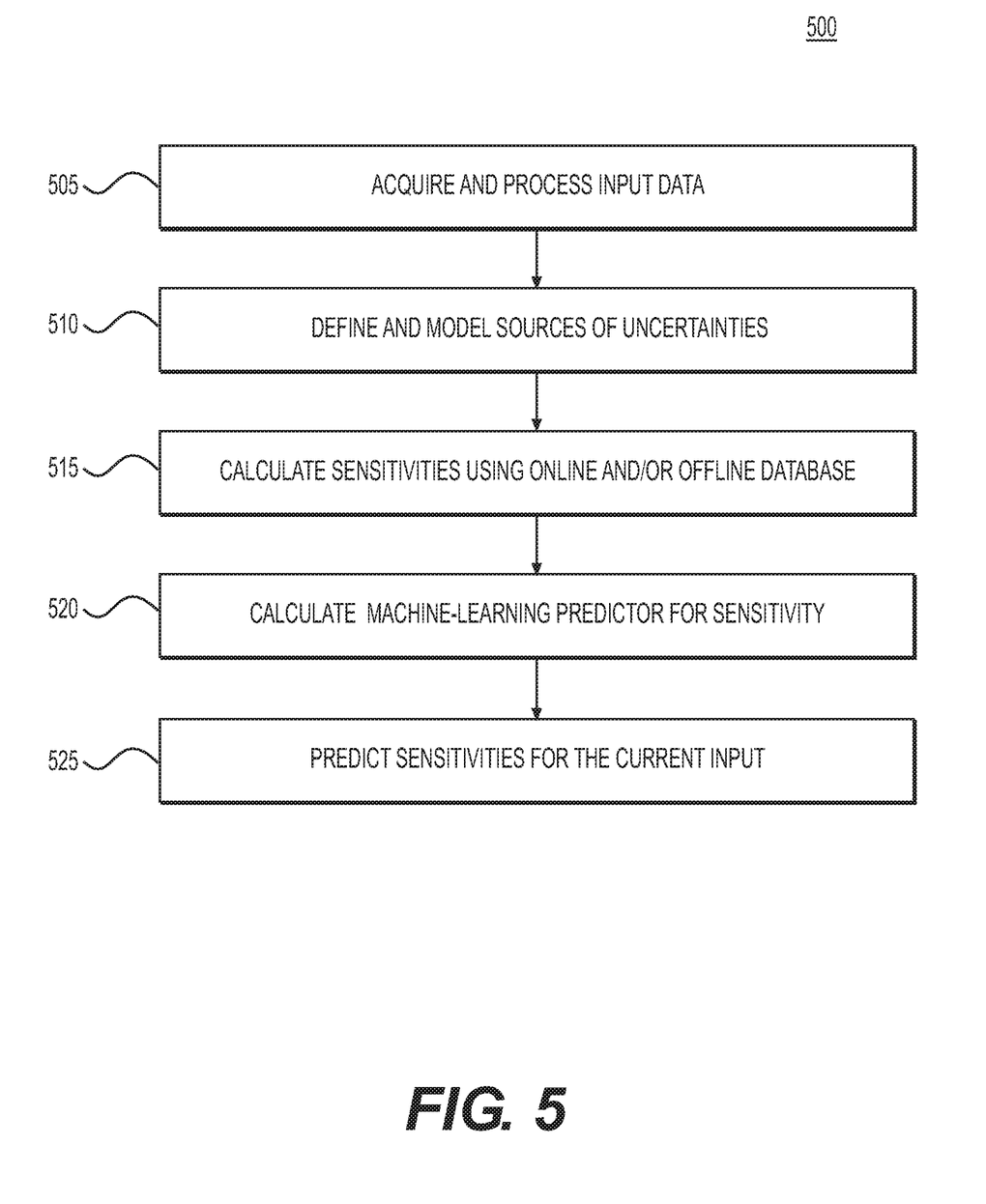
FIG. 5 is a flow chart that describes an exemplary process for sensitivity prediction of growth and remodeling response to the geometry of a stented artery, according to an exemplary embodiment of the present disclosure.

FIG. 5 is now discussed, which shows a flow chart describing an exemplary process for sensitivity prediction of growth and remodeling response to the geometry of a stented artery (post stent deployment). The stenting procedure affects near-wall hemodynamics including wall shear stress and intramural stress, which in turn affects propensity for re-stenosis. As shown in the embodiment 500, sources of uncertainties associated with a digital representation may be determined, and machine learning, or other algorithms, may be used to predict one or more sensitivities.

As shown in step 505, input data may be acquired and/or processed. An MRI or CT scan, for example, may be acquired of a patient who is a candidate for a stenting operation including the aorta and arteries of interest encompassing the stenting location. One or more stent deployment plans including location and intended shape of the artery post-surgery may also be acquired and/or processed.

The sources of uncertainties may be defined and/or modeled, as shown in step 510. For example, uncertainty in the stent deployment geometry may be defined and modeled. Due to uncertainty associated with the location and shape of the stenting procedure, the lumen geometry post-surgery of a stented vessel may be uncertain. An expected shape of the lumen post-surgery may be calculated based on the stent deployment plan (the diameter to which the balloon is inflated and the precise location). The standard deviation in the stent location and diameter may be estimated to be a fraction of the mean expected parameters, where the fraction is patient and lesion specific (for e.g., ostial/non-ostial lesions).

Clinical parameters that are relevant to the simulations may be assumed to be uncertain with either a uniform or Gaussian distribution. Uncertainties for hemodynamic simulations include measured blood pressure, body mass index, blood viscosity, and/or downstream perfusion indices if available. Some of these uncertainties for arterial growth and remodeling simulations may include (i) the constitutive material property of the wall, (ii) the stretch at which components such as elastin and collagen are deposited, and/or (iii) gain parameters, which determine the response of vessel wall to deviations in stress from homeostatic values.

As shown in step 515, the sensitivity may be calculated using at least one online and/or offline database. This step may be performed for a large database (say 100 stented geometries) so that they capture patient-to-patient variability such as lesions in different locations, vessels of different caliber and length, etc.

There are typically two sets of governing equations that may be solved in a coupled fashion. Blood flow rate and pressures in the stented lumen may be calculated based on estimated stented geometry by solving Navier-Stokes equations. Intramural and shear stresses may be estimated from these, and may be used to predict growth and remodeling response after which they are run for an extended time, such as one or more days. The new geometry may be fed back to the Navier-Stokes equation from which updated wall shear stress and intramural stresses are estimated, and so on. The simulation may be terminated after sufficient time (typically months or years) to estimate remodeled state and the propensity for re-stenosis. Simulation of growth and remodeling may be performed by solving quasi-static stress equilibrium equations, and accounting for the addition and removal of material to the wall during remodeling process. These simulations are computationally expensive, and might take significant time to solve.

The sensitivity may also be calculated using stochastic collocation. A stochastic shape space may be defined that describes uncertainty in stent deployment geometry. Specific instances of the stented geometry may be identified at quadrature points of the stochastic space using the stochastic collocation algorithm. Following this, hemodynamic, growth and/or remodeling simulations may be performed at each collocation point as described above. The wall shear stress and intramural stress after sufficient time (a few years) may be calculated throughout the stochastic space using an interpolation such as a Lagrange polynomial interpolation. A histogram may be constructed by sampling the stochastic space according to the input probability defined in step 510, from which sensitivity values may be calculated.

A machine learning predictor for sensitivity may be calculated, as discussed in step 520. Regarding input features, for each of the stented geometries, one or more of the following set of input features may be calculated: (i) parameters of the geometry, (ii) hemodynamic indices, (iii) the magnitude of input uncertainty, (iv) the material properties of the vessel wall, and/or (v) the parameters driving the dynamics of growth and remodeling. Regarding the parameters of the geometry, the following may be calculated: pre-stented and post-stented lumen area, lumen diameter, volume of blood upstream and downstream in the computational model, distance to nearest branch upstream and downstream of the stented location, min/max/mean upstream and downstream diameter, distance to minimum upstream and downstream diameter, min/max/mean outlet resistances, and geometric resistance using, for example, the Poiseulle equation.

Hemodynamic indices may also be calculated, such as flow rates, pressure drops, FFR using Poiseulle's equation, and kinetic energy drop in the pre-stented geometry and planned stented configuration. A pressure recovery factor may be calculated, and may be defined as the ratio of downstream to upstream area if this ratio is >1.2 (although this pre-determined ratio may vary) and included in the feature vector.

The magnitude of input uncertainty that was defined for each entity in step 515 may also be calculated. The material properties of the vessel wall such as collagen, elastin, and smooth muscle cell may also be calculated. Further, parameters driving dynamics of growth and remodeling, such as the half-life of different constituents, pre-stretch of deposited constituents, and gain parameters, defined as the ratio between the mass of constituent added and deviation of stress from homeostatic values, may also be calculated.

The database may be divided into a 66% training set and 34% test set, although this pre-determined ratio may vary. A decision tree or a polynomial regressor may be computed that maps the features identified in step 520 to the sensitivities calculated in step 515, so that predictive error is minimized. The resulting predictor may be stored in digital form (e.g. disc, laptop, hard-drive, network drive, etc.).

As discussed in step 525, the sensitivities for current input may be predicted. The sensitivities for the data stored in step 505 may be predicted by calculating all the features identified in step 520, and using the stored machine learning predictor (step 520) to calculate sensitivities through the patient specific model.

The solution may be mapped and displayed. The sensitivity of the quantities of interest to geometry through the vessel of interest may be displayed on a device. This could be used to ensure the fidelity and accuracy of stent deployment at highly sensitive regions.

Figure 6:
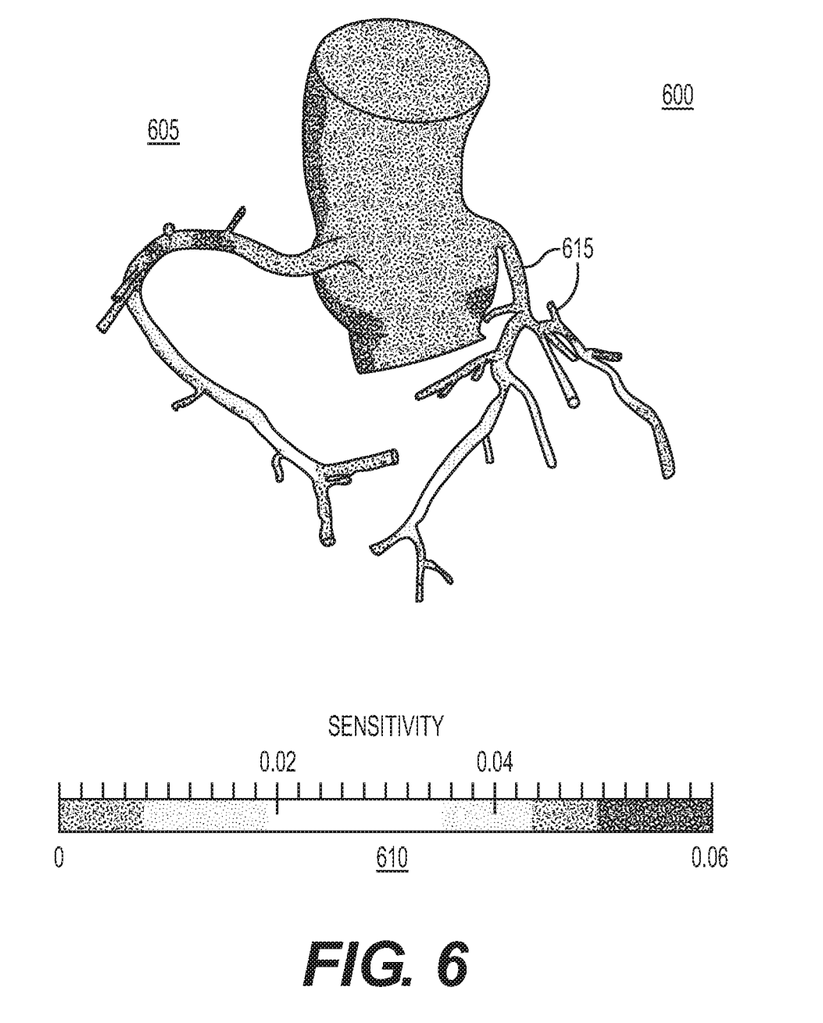
FIG. 6 is a diagram illustrating an exemplary sensitivity map calculated using machine learning, according to an exemplary embodiment of the present disclosure.

FIG. 6. depicts a diagram illustrating an exemplary sensitivity map 600 calculated using machine learning according to an exemplary embodiment of the present disclosure. As discussed above, centerline points may be chosen to define a segment. For example, in reference to the first specific embodiment presented above, a spatial resolution of 3 mm could be achieved if the distance between centerline points is 0.5 mm. A sensitivity map display 605 may be shown to a physician and/or user with a sensitivity scale 610 to allow a physician and/or user to interpret the display. The sensitivity scale 610 may display colors or otherwise provide indicators as to the sensitivity values of different portions of a structure such as, for example, a patient's coronary arteries. Colors of other indicators 615 may be projected onto the display corresponding to different sensitivity values. This means that each color or other indicator 615 may indicate the sensitivity of the blood flow calculations to changes or uncertainty in the geometry. This is important and/or useful because the technician or physician knows where to focus his or her efforts.

Figure 7:
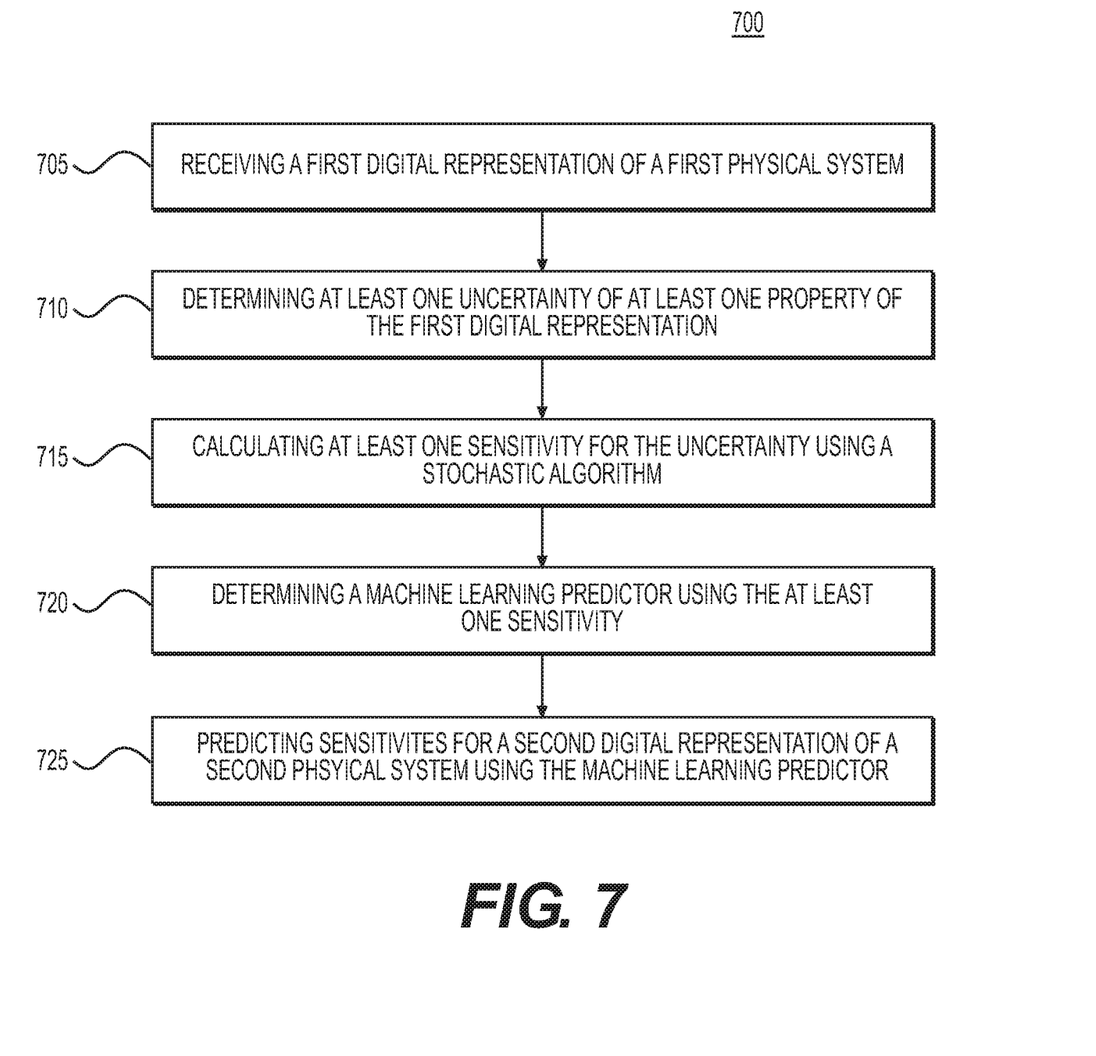
FIG. 7 is a flow chart that describes an exemplary process for geometric sensitivity prediction, according to an exemplary embodiment of the present disclosure.

FIG. 7 is a flow chart that describes an exemplary process for geometric sensitivity prediction according to an exemplary embodiment of the present disclosure. At step 705, a first digital representation of a first physical system is received. At step 710, at least one uncertainty of at least one property of the first digital representation is determined. At step 715, at least one sensitivity is calculated for the uncertainty using a stochastic algorithm. At step 720, a machine learning predictor utilizing a plurality of patients is determined. At step 725, sensitivities for a second digital representation of a second physical system using the machine learning predictor are predicted.

As a result of embodiments discussed herein, a technician and/or physician may be able to predict the sensitivities of blood flow or other properties to uncertainty in an input digital representation. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A computer-implemented method of determining a sensitivity of a patient's blood flow characteristic to uncertainty in a geometric model of a patient's vascular system, the method comprising:
   obtaining, for each of a plurality of individuals, a geometric model of at least a portion of a vascular system of each individual;
   calculating, for each geometric model, at least one sensitivity of a blood flow characteristic to at least one uncertainty in geometry in the geometric model;
   identifying a plurality of features of each geometric model;
   mapping, in a machine learning database, the identified features to the calculated sensitivities;
   generating, for a patient, a geometric model of at least part of the patient's vascular system using patient-specific imaging data of at least a portion of the patient's vascular system;
   determining, for the patient, a blood flow characteristic, at least one feature, and at least one value of uncertainty in geometry in the geometric model of at least part of the patient's vascular system; and
   determining a sensitivity of the blood flow characteristic of the patient to the at least one value of uncertainty in geometry in the geometric model of at least part of the patient's vascular system, using the at least one feature and the machine learning database.

2. The method of claim 1, wherein calculating, for each geometric model, the at least one sensitivity of a blood flow characteristic to the at least one uncertainty in geometry in the geometric model comprises assigning a probabilistic distribution function to the at least one uncertainty.

3. The method of claim 1, wherein calculating, for each geometric model, the at least one sensitivity of the blood flow characteristic to the at least one uncertainty in geometry in the geometric model comprises solving a stochastic algorithm for a vessel region in the geometric model.

4. The method of claim 3, wherein solving the stochastic algorithm comprises utilizing quadrature points identified by a Smolyak sparse grid algorithm.

5. The method of claim 3, further comprising creating a decision tree using the mapped identified features and the calculated sensitivities in the machine learning database, and wherein determining the sensitivity of the blood flow characteristic of the patient to the at least one value of uncertainty further comprises using the decision tree.

6. The method of claim 1, wherein determining the sensitivity of the blood flow characteristic of the patient comprises identifying a mapped identified feature among the identified features in the machine learning database, the mapped identified feature corresponding to the at least one feature for the patient.

7. The method of claim 1, further comprising splitting the mapped identified features and the calculated sensitivities in the machine learning database into a training set and a test set.

8. A system for determining a sensitivity of a patient's blood flow characteristic to uncertainty in a geometric model of a patient's vascular system, the system comprising:
   a data storage device storing instructions for determining sensitivity; and
   a processor configured to execute the instructions to perform a method including the steps of:
      obtaining, for each of a plurality of individuals, a geometric model of at least a portion of a vascular system of each individual;
      calculating, for each geometric model, at least one sensitivity of a blood flow characteristic to at least one uncertainty in geometry in the geometric model;
      identifying a plurality of features of each geometric model;
      mapping, in a machine learning database, the identified features to the calculated sensitivities;
      generating, for a patient, a geometric model of at least part of the patient's vascular system using patient-specific imaging data of at least a portion of the patients' vascular system;
      obtaining, for the patient, a blood flow characteristic, at least one feature, and at least one value of uncertainty in geometry in the geometric model of at least part of the patient's vascular system; and
      determining a sensitivity of the blood flow characteristic of the patient to the at least one value of uncertainty in geometry in the geometric model of at least part of the patient's vascular system, using the at least one feature and the machine learning database.

9. The system of claim 8, wherein calculating, for each geometric model, the at least one sensitivity of a blood flow characteristic to the at least one uncertainty in geometry in the geometric model comprises assigning a probabilistic distribution function to the at least one uncertainty.

10. The system of claim 8, wherein calculating, for each geometric model, the at least one sensitivity of the blood flow characteristic to the at least one uncertainty in geometry in the geometric model comprises solving a stochastic algorithm for a vessel region in the geometric model.

11. The system of claim 10, wherein solving the stochastic algorithm comprises utilizing quadrature points identified by a Smolyak sparse grid algorithm.

12. The system of claim 10, wherein, for each geometric model, a resolution of the sensitivity may be increased by solving a stochastic algorithm for an increased number of vessel regions of the geometric model.

13. The system of claim 8, wherein the processor is further configured to determine the sensitivity of the blood flow characteristic of the patient by identifying a mapped identified feature among the identified features in the machine learning database, the mapped identified feature corresponding to the at least one feature for the patient.

14. The system of claim 8, wherein the processor is further configured to split the mapped identified features and the calculated sensitivities in the machine learning database into a training set and a test set.

15. A non-transitory computer readable medium for use on at least one computer system containing computer-executable programming instructions for determining a sensitivity of a patient's blood flow characteristic to uncertainty in a geometric model of a patient's vascular system, the instructions comprising steps for:
- obtaining, for each of a plurality of individuals, a geometric model of at least a portion of a vascular system of each individual;
- calculating, for each geometric model, a sensitivity of at least one blood flow characteristic to at least one uncertainty in geometry in the geometric model;
- identifying a plurality of features of each geometric model;
- mapping, in a machine learning database, the identified features to the calculated sensitivities;
- generating, for a patient, a geometric model of at least part of the patient's vascular system using patient-specific imaging data of at least a portion of the patient's vascular system;
- determining, for the patient, a blood flow characteristic, at least one feature, and at least one value of uncertainty in geometry in the geometric model of at least part of the patient's vascular system; and
- determining a sensitivity of the blood flow characteristic of the patient to the at least one value of uncertainty in geometry in the geometric model of at least part of the patient's vascular system, using the at least one feature and the machine learning database.

16. The computer readable medium of claim 15, wherein calculating, for each geometric model, the at least one sensitivity of a blood flow characteristic to the at least one uncertainty in geometry in the geometric model comprises assigning a probabilistic distribution function to the at least one uncertainty.

17. The computer readable medium of claim 15, wherein calculating, for each geometric model, the at least one sensitivity of the blood flow characteristic to the at least one uncertainty in geometry in the geometric model comprises solving a stochastic algorithm for a vessel region of the geometric model.

18. The computer readable medium of claim 17, wherein solving the stochastic algorithm comprises utilizing quadrature points identified by a Smolyak sparse grid algorithm.

19. The computer readable medium of claim 17, wherein, for each geometric model, a resolution of the at least one sensitivity may be increased by solving a stochastic algorithm for an increased number of vessel regions of the geometric model.

20. The computer readable medium of claim 15, wherein determining the sensitivity of the blood flow characteristic of the patient comprises identifying a mapped identified feature among the identified features in the machine learning database, the mapped identified feature corresponding to the at least one feature for the patient.

* * * * *